United States Patent
Li

(10) Patent No.: US 11,624,094 B2
(45) Date of Patent: Apr. 11, 2023

(54) COMPOSITIONS AND METHODS FOR DIAGNOSING AND TREATING DEGENERATIVE MITRAL VALVE DISEASE IN A CANINE

(71) Applicant: Societe des Produits Nestle SA, Vevey (CH)

(72) Inventor: Qinghong Li, Chesterfield, MO (US)

(73) Assignee: SOCIETE DES PRODUITS NESTLE S.A., Vevey (CH)

( * ) Notice: Subject to any disclaimer, the term of this patent is extended or adjusted under 35 U.S.C. 154(b) by 555 days.

(21) Appl. No.: 16/716,842

(22) Filed: Dec. 17, 2019

(65) Prior Publication Data

US 2020/0206281 A1     Jul. 2, 2020

Related U.S. Application Data

(60) Provisional application No. 62/785,373, filed on Dec. 27, 2018.

(51) Int. Cl.
| | |
|---|---|
| *C12Q 1/689* | (2018.01) |
| *A23K 50/40* | (2016.01) |
| *A23K 10/16* | (2016.01) |
| *A61K 35/742* | (2015.01) |

(52) U.S. Cl.
CPC .............. *C12Q 1/689* (2013.01); *A23K 10/16* (2016.05); *A23K 50/40* (2016.05); *A61K 35/742* (2013.01)

(58) Field of Classification Search
None
See application file for complete search history.

(56) References Cited

U.S. PATENT DOCUMENTS

| | | |
|---|---|---|
| 2016/0237495 A1 | 8/2016 | Li |
| 2018/0064140 A1 | 3/2018 | Li |

FOREIGN PATENT DOCUMENTS

| | | |
|---|---|---|
| CA | 3045026 A1 | 6/2018 |
| WO | 2013154826 A2 | 10/2013 |

OTHER PUBLICATIONS

International Search Report and Written Opinion to Application No. PCT/IB2019/060939 dated Jun. 23, 2020.

*Primary Examiner* — Michelle F. Paguio Prising

(57) ABSTRACT

The present invention relates to methods and compositions for diagnosing and treating degenerative mitral valve disease in a canine. In one embodiment, a method of diagnosing early stage degenerative mitral valve disease in a canine can comprise measuring a normalized relative abundance of a biomarker selected from the group consisting of *Erysipelatoclostridium*, *Ruminococcaceae* UCG014, *Butyricicoccus*, *Faecalibacterium*, and combinations thereof, and determining that the canine has early stage degenerative mitral valve disease if the *Erysipelatoclostridium* is from 0 to 0.5 normalized relative abundance, the *Ruminococcaceae* UCG014 is from 0 to 0.1 normalized relative abundance, the *Butyricicoccus* is from 0 to 0.1 normalized relative abundance, or the *Faecalibacterium* is from 0 to 0.1 normalized relative abundance.

9 Claims, No Drawings

COMPOSITIONS AND METHODS FOR DIAGNOSING AND TREATING DEGENERATIVE MITRAL VALVE DISEASE IN A CANINE

CROSS REFERENCE TO RELATED APPLICATIONS

This application claims priority to U.S. Provisional Application No. 62/785,373 filed Dec. 27, 2018, the disclosure of which is incorporated herein by this reference.

BACKGROUND

Canine degenerative mitral valve disease (DMVD) is characterized by slowly progressive valvular degeneration that causes mitral regurgitation and, in some dogs, congestive heart failure (CHF). Although dogs in the early stage typically have a lengthy preclinical period, once progressed to the stage with CHF, the disease advances more rapidly with a mean survival time less than 12 months. Thus, it is of great interest to intervene at the early preclinical stage to extend the longevity of affected dogs. In recent years, a staging scheme for classifying canine DMVD has been adopted by the consensus committee established by the American College of Veterinary Internal Medicine (ACVIM). Dogs at risk of developing DMVD but otherwise healthy are considered stage A; dogs with a heart murmur due to mitral regurgitation but without clinical signs of CHF are classified as stage B; dogs with overt clinical signs of CHF are classified as stage C. Stage B dogs are further divided into stage B1 or B2 due to the absence or presence of cardiac remodeling.

Currently, the only medication that has been proven to be effective for early preclinical DMVD is pimobanden, which, like any pharmaceutical drug, comes with side effects. Currently, the gold standard for DMVD diagnosis is echocardiogram, which is not only expensive but also requires highly specialized veterinary cardiologist. As such, effective diagnostic methods and treatments overcoming the disadvantages of current methods and treatments continue to be sought.

SUMMARY

The present disclosure relates generally to compositions and methods for diagnosing and treatment degenerative mitral valve disease in a canine. In one embodiment, a method of diagnosing early stage degenerative mitral valve disease in a canine can comprise measuring a normalized relative abundance of a biomarker selected from the group consisting of *Erysipelatoclostridium, Ruminococcaceae* UCG014, *Butyricicoccus, Faecalibacterium*, and combinations thereof, and determining that the canine has early stage degenerative mitral valve disease if the *Erysipelatoclostridium* is from 0 to 0.5 normalized relative abundance, the *Ruminococcaceae* UCG014 is from 0 to 0.1 normalized relative abundance, the *Butyricicoccus* is from 0 to 0.1 normalized relative abundance, or the *Faecalibacterium* is from 0 to 0.1 normalized relative abundance.

In another embodiment, a method of treating or slowing progression of degenerative mitral valve disease in a canine can comprise administering a composition to the canine, wherein the composition comprises a probiotic selected from the group consisting of *Butyricicoccus* and *Faecalibacterium*.

In another embodiment, a pet food can comprise protein, fat, carbohydrate, fiber, and a probiotic selected from the group consisting of *Butyricicoccus, Faecalibacterium*, and combinations thereof.

Additional features and advantages are described herein and will be apparent from the following Detailed Description

DETAILED DESCRIPTION

Definitions

As used in this disclosure and the appended claims, the singular forms "a," "an" and "the" include plural referents unless the context clearly dictates otherwise. Thus, for example, reference to "a composition" or "the composition" includes two or more compositions. The term "and/or" used in the context of "X and/or Y" should be interpreted as "X," or "Y," or "X and Y." Where used herein, the terms "example" and "such as," particularly when followed by a listing of terms, are merely exemplary and illustrative, and are not exclusive or comprehensive.

As used herein, "about" is understood to refer to numbers in a range of numerals, for example the range of −10% to +10% of the referenced number, within −5% to +5% of the referenced number, or in one aspect, within −1% to +1% of the referenced number, and in a specific aspect, within −0.1% to +0.1% of the referenced number. Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed. When reference is made to the pH, values correspond to pH measured at 25° C. with standard equipment. An "amount" can be the total amount of the referenced component per serving of the composition or per distinct unit of the composition and/or can be the weight percentage of the referenced component by dry weight. Moreover, an "amount" includes zero; for example, the recitation of an amount of a compound does not necessarily mean that the compound is present, unless followed by a range that excludes zero.

The terms "food," "food product" and "food composition" mean a product or composition that is intended for ingestion by an animal and provides at least one nutrient to the animal. Further in this regard, these terms mean that the product or composition is in a form ready for consumption and is not merely an intermediate from which a consumable product or composition is made, although other food compositions can be added in some embodiments. The term "pet food" means any food composition intended to be consumed by a pet. The term "pet" means any animal which could benefit from or enjoy the compositions provided by the present disclosure. For example, the pet can be an avian, bovine, canine, equine, feline, hircine, lupine, murine, ovine, or porcine animal, but the pet can be any suitable animal.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO).

The term "companion animal" means a dog or a cat. In an embodiment, the compositions and methods disclosed herein involve a senior dog. Dogs are considered senior in the last 25% of their lives. The life span of a dog depends on its size and/or its breed, but for the present disclosure a senior dog is a dog that is at least 5 years of age (e.g., at least 6 years of age, at least 7 years of age, or at least 8 years of age).

As used herein, "normalized relative abundance" refers to the amount of each microorganism calculated by taking each count and dividing by the total sequence count in each sample and transforming by square root.

As used herein, "early stage degenerative mitral valve disease" refers to stage B of degenerative mitral valve disease.

As used herein, "stage A" refers to dogs that are at risk of developing degenerative mitral valve disease, but otherwise have a healthy heart.

As used herein, "stage B" refers to dogs with a heart murmur due to mitral regurgitation but without clinical signs of congestive heart failure. "Stage B" includes stage B1 (absence of cardiac remodeling and stage B2 (presence of cardiac remodeling).

As used herein, stage C" refer to dogs having congestive heart failure.

As used herein, "degenerative mitral valve disease," "DMVD," "myxomatous mitral valve disease," and "MMVD" can be used interchangeably and refers to progressive valvular degeneration that causes mitral regurgitation and/or congestive heart failure (CHF) and includes stage A, stage B, and stage C.

A "blended" composition merely has at least two components having at least one different characteristic relative to each other, preferably at least moisture content and water activity in the context of the present disclosure. In this regard, description of a composition as "blended" does not imply that the blended composition has been subjected to processing sometimes referenced as "blending," namely mixing components so that they are indistinguishable from each other, and, in one aspect, such processing is avoided when mixing one component with the other components to form a blended composition (e.g., mixing a dry component with a wet or semi-moist component). Further in this regard, in a blended composition each of the at least two components having at least one different characteristic relative to each other preferably retain their distinct identity and appearance.

"Wet food" means a pet food having a moisture content from about 50% to about 90%, and in one aspect, from about 70% to about 90%. "Dry food" means a pet food having a moisture content less than about 20%, and in one aspect, less than about 15%, and in a specific aspect, less than about 10%. "Semi-moist food" means a pet food having a moisture content from about 20% to about 50%, and in one aspect, from about 25% to about 35%.

"Kibbles" is used synonymously with "chunks" herein and both terms mean pieces of dry or semi-moist pet food which can have a pellet shape or any other shape and can be made by slicing a food composition into separate pieces. Non-limiting examples of kibbles include particulates; pellets; pieces of pet food, dehydrated meat, meat analog, vegetables, and combinations thereof; and pet snacks, such as meat or vegetable jerky, rawhide, and biscuits. A "meat analog" is a meat emulsion product that resembles pieces of natural meat in appearance, texture, and physical structure.

The term "effective amount" of "therapeutically effect amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In some aspects, the particular disease, condition, or disorder can be degenerative mitral valve disease.

The term "dietary supplement" means a product that is intended to be ingested in addition to the normal animal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging animals, the animal will continue consuming on a regular basis for the remainder of its life. This can also be referred to as consumption for "extended" periods.

The term "regular basis" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption.

The dosages expressed herein are in milligrams per kilogram of body weight per day (mg/kg/day) unless expressed otherwise.

The compositions disclosed herein may lack any element that is not specifically disclosed herein. Thus, a disclosure of an embodiment using the term "comprising" includes a disclosure of embodiments "consisting essentially of" and "consisting of" the components identified. Similarly, the methods disclosed herein may lack any step that is not specifically disclosed herein. Thus, a disclosure of an embodiment using the term "comprising" includes a disclosure of embodiments "consisting essentially of" and "consisting of" the steps identified. Any embodiment disclosed herein can be combined with any other embodiment disclosed herein unless explicitly and directly stated otherwise.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, are relevant prior art for the present invention and the right to challenge the accuracy and pertinence of such patents, patent applications, publications, and other references is specifically reserved.

Embodiments

In one embodiment, a method of diagnosing early stage degenerative mitral valve disease in a canine can comprise measuring a normalized relative abundance of a biomarker selected from the group consisting of *Erysipelatoclostridium*, *Ruminococcaceae* UCG014, *Butyricicoccus*, *Faecalibacterium*, and combinations thereof, and determining that the canine has early stage degenerative mitral valve disease if the *Erysipelatoclostridium* is from 0 to 0.5 normalized relative abundance, the *Ruminococcaceae* UCG014 is from 0 to 0.1 normalized relative abundance, the *Butyricicoccus* is from 0 to 0.1 normalized relative abundance, or the *Faecalibacterium* is from 0 to 0.1 normalized relative abundance.

Generally, diagnosing of early stage degenerative mitral valve disease can be based on a measurement of anyone of *Erysipelatoclostridium*, *Ruminococcaceae* UCG014, *Butyricicoccus*, and *Faecalibacterium*. However, in one aspect, diagnosing can be determined based on *Erysipelatoclostridium*. In another aspect, diagnosing can be determined based on *Ruminococcaceae* UCG014. In still another aspect, diagnosing can be determined based on *Butyricicoccus*. In yet another aspect, diagnosing can be determined based on *Faecalibacterium*. Further, in one embodiment, diagnosing can be determined based on two biomarkers. In another embodiment, diagnosing can be determined based on three biomarkers. In still another embodiment, diagnosing can be determined based on all four types of biomarkers.

Generally, such biomarkers can include any species within the genus. However, in one aspect, the *Butyricicoccus* can be *Butyricicoccus* spp. In another aspect, the *Faecalibacterium* can be *Faecalibacterium prausnitzii*.

In another embodiment, a method of treating or slowing progression of degenerative mitral valve disease in a canine can comprise administering a composition to the canine, wherein the composition comprises a probiotic selected from the group consisting of *Butyricicoccus* and *Faecalibacterium*. As discussed herein in one aspect, the *Butyricicoccus* can be *Butyricicoccus* spp. In another aspect, the *Faecalibacterium* can be *Faecalibacterium prausnitzii*.

Generally, the probiotic is generally present in a therapeutically effective amount. In one aspect, the probiotic can be present in an amount of $10^5$ to $10^{12}$ colony forming units (cfu). In other aspects, the probiotic can be present in an amount of $10^5$ to $10^9$, $10^7$ to $10^9$, $10^9$ to $10^{11}$, or even $10^9$ to $10^{12}$. Generally, the composition can be administered sufficiently such that the treatment is effective. In one aspect, the administration can be on a regular basis. In another aspect, the administration can be a long-term administration.

Administration of the composition can include any manner of delivery. In one embodiment, the composition can be administered in conjunction with a pet food composition. In another embodiment, the composition is a pet food. In still another embodiment, the composition can be a sachet or supplement administered in conjunction with a pet food. In yet another embodiment, the composition can be a sachet or supplement administered separately from other food compositions.

In another embodiment, a pet food can comprise protein, fat, carbohydrate, fiber, and a probiotic selected from the group consisting of *Butyricicoccus*, *Faecalibacterium*, and combinations thereof. As discussed herein in one aspect, the *Butyricicoccus* can be *Butyricicoccus* spp. In another aspect, the *Faecalibacterium* can be *Faecalibacterium prausnitzii*. As discussed herein, the probiotic is generally present in a therapeutically effective amount. In one aspect, the probiotic can be present in an amount of $10^5$ to $10^{12}$ colony forming units (cfu). In other aspects, the probiotic can be present in an amount of $10^5$ to $10^9$, $10^7$ to $10^9$, $10^9$ to $10^{11}$, or even $10^9$ to $10^{12}$.

As discussed herein, the pet food can comprise the probiotic as a single composition or can be provided in multiple compositions that can be administered in conjunction or separately. In one embodiment, the pet food composition can comprise a packaged pet food and packaged probiotic that can be added to the pet food. In another embodiment, the pet food can comprise the probiotic formulated therein as a single composition.

The present pet food compositions generally are complete and balanced pet foods for a canine. In various embodiments, pet food compositions can comprise from about 15% to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include pork, lamb, equine, poultry, fish, and mixtures thereof.

The compositions may further comprise from about 5% to about 40% fat. The compositions may further comprise a source of carbohydrate. The compositions may comprise from about 15% to about 60% carbohydrate. Examples of such carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products.

In some embodiments, the ash content of the composition ranges from less than 1% to about 15%, and in one aspect, from about 5% to about 10%.

The moisture content can vary depending on the nature of the composition. In one embodiment, the composition can be a complete and nutritionally balanced pet food. In this embodiment, the pet food may be a "wet food", "dry food", or food of intermediate moisture content. "Wet food" describes pet food that is typically sold in cans or foil bags, and has a moisture content typically in the range of about 50% to about 90%, and in one aspect, 70% to 90%. "Dry food" describes pet food which is of a similar composition to wet food, but contains a limited moisture content, typically in the range of about 5% to about 15% or 20%, and therefore is presented, for example, as small biscuit-like kibbles. In one embodiment, the compositions can have moisture content from about 5% to about 20%. Dry food products include a variety of foods of various moisture contents, such that they are relatively shelf-stable and resistant to microbial or fungal deterioration or contamination. Also included are dry food compositions which are extruded food products, such as pet foods, or snack foods for either humans or companion animals. "Semi-moist food" means a pet food having a moisture content from about 20% to about 50%, and in one aspect, from about 25% to about 35%.

The compositions may also comprise one or more fiber sources. The term "fiber" includes all sources of "bulk" in the food whether digestible or indigestible, soluble or insoluble, fermentable or nonfermentable. Fibers can be from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefit provided by the present invention to the immune system of an animal.

In each of these compositions and methods, the pet food composition can be a wet food, a semi-moist food or a dry food. In an embodiment, the pet food composition can be one or more components of a blended composition. In some embodiments, the pet food composition is a kibble, and in some embodiments, the pet food composition is a meat analog.

The pet food compositions disclosed herein can comprise vegetable oil, a flavorant, a colorant and water. Suitable vegetable oils include soybean oil, corn oil, cottonseed oil, sunflower oil, canola oil, peanut oil, safflower oil, and the like. Examples of suitable flavorants include yeast, tallow, rendered animal meals (e.g., poultry, beef, lamb, pork), flavor extracts or blends (e.g., grilled beef), animal digests, and the like. Suitable colorants include FD&C colors, such as blue no. 1, blue no. 2, green no. 3, red no. 3, red no. 40, yellow no. 5, yellow no. 6, and the like; natural colors, such as caramel coloring, annatto, chlorophyllin, cochineal, betanin, turmeric, saffron, paprika, lycopene, elderberry juice, pandan, butterfly pea and the like; titanium dioxide; and any suitable food colorant known to the skilled artisan.

The pet food compositions disclosed herein can optionally include additional ingredients, such as other grains and/or other starches additionally or alternatively to flour, amino acids, fibers, sugars, animal oils, aromas, other oils additionally or alternatively to vegetable oil, humectants, preservatives, polyols, salts, oral care ingredients, antioxidants, vitamins, minerals, probiotic microorganisms, bioactive molecules or combinations thereof.

Suitable starches include a grain such as corn, rice, wheat, barley, oats, soy and the like, and mixtures of these grains, and can be included at least partially in any flour. Suitable humectants include salt, sugars, propylene glycol and polyhydric glycols such as glycerin and sorbitol, and the like. Suitable oral care ingredients include alfalfa nutrient concentrate containing chlorophyll, sodium bicarbonate, phosphates (e.g., tricalcium phosphate, acid pyrophosphates, tetrasodium pyrophosphate, metaphosphates, and orthophosphates), peppermint, cloves, parsley, ginger and the like. Examples of suitable antioxidants include butylated hydroxyanisole ("BHA") and butylated hydroxytoluene ("BHT"), vitamin E (tocopherols), and the like.

Non-limiting examples of vitamins that can be used include Vitamins A, B-complex (such as B-1, B-2, B-6 and B-12), C, D, E and K, niacin and acid vitamins such as pantothenic acid and folic acid and biotin. Non-limiting examples of suitable minerals include calcium, iron, zinc, magnesium, iodine, copper, phosphorus, manganese, potassium, chromium, molybdenum, selenium, nickel, tin, silicon, vanadium, boron and the like.

As discussed herein, the compositions can further comprise prebiotics or other probiotics. Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Prebiotics are nondigestible food ingredients that beneficially affect host health by selectively stimulating the growth and/or activity of bacteria in the colon. Prebiotics include fructooligosaccharides (FOS), xylooligosaccharides (XOS), galactooligosaccharides (GOS), and mannooligosaccharides (typically for non-human foods such as pet foods). The prebiotic, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of bifidobacteria in the colon, increasing calcium absorption, increasing fecal weight, shortening of gastrointestinal transit time, and possibly lowering blood lipid levels. Probiotics enhance systemic cellular immune responses and may be useful as a dietary supplement to boost natural immunity in otherwise healthy adults, or provide other benefits as discussed herein. Generally known probiotics include many types of bacteria but generally are selected from four genera of bacteria: *Lactobacilllus acidophillus, Bifidobacteria, Lactococcus*, and *Pediococcus*. Beneficial species include *Enterococcus* and *Saccharomyces* species. The amount of probiotics and prebiotics to be administered to the animal is determined by the skilled artisan based upon the type and nature of the prebiotic and probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, and in one aspect, from about 5 billion to about 10 billion live bacteria per day. Generally, prebiotics are administered in amounts sufficient to positively stimulate the healthy microflora in the gut and cause these "good" bacteria to reproduce. Typical amounts are from about one to about 10 grams per serving or from about 5% to about 40% of the recommended daily dietary fiber for an animal. The probiotics and prebiotics can be made part of the composition by any suitable means. For example, the agents can be mixed with the composition or applied to the surface of the composition, e.g., by sprinkling or spraying. When the agents are part of a kit, the agents can be admixed with other materials or in their own package.

Non-limiting examples of suitable preservatives include potassium sorbate, sorbic acid, sodium methyl para-hydroxybenzoate, calcium propionate, propionic acid, and combinations thereof.

Specific amounts for each additional ingredient in the pet food compositions disclosed herein will depend on a variety of factors such as the ingredient included in the first edible material and any second edible material; the species of animal; the animal's age, body weight, general health, sex, and diet; the animal's consumption rate; the purpose for which the food product is administered to the animal; and the like. Therefore, the components and their amounts may vary widely.

For example, the amount of any of the above-noted ingredients can be decreased or increased based on the estimated effect on degenerative mitral valve disease.

EXAMPLES

The following non-limiting examples are illustrative of embodiments of the present disclosure.

Example 1—MMVD Study of Canines

Fecal samples from four groups of dogs were collected: group 1, dogs with no evidence of cardiac disease; group 2, dogs with stage B1 myxomatous mitral valve disease (MMVD); group 3, dogs with stage B2 MMVD; and group 4, dogs with stage C MMVD. Dogs were examined and classified based on physical examination and echocardiogram by board certified veterinary cardiologists according to the consensus statements from the American College of Veterinary Internal Medicine (ACVIM). Dogs in the four groups were matched by age, sex, body condition score (BCS). Dogs with the following conditions were excluded: 1) received antibiotics within the last 60 days, 2) with active diarrhea or vomiting, 3) with major systemic diseases such as cancer, diabetes mellitus, renal failure, or systemic hypertension, 4) Congenital heart disease and other cardiac abnormalities, 5) BCS greater than or equal to 8 or less than or equal to 3, 6) younger than 7. History of medication was recorded.

Fresh feces were collected within 30 minutes of defecation and brought to the laboratory in 6 hours. Three aliquots of 1-2 grams from each dog were stored in −80 C freezer until use.

Fecal DNA was extracted using PowerFecal DNA isolation kit (MO BIO Laboratories, Inc, Carlsbad, Calif.) following manufacturer's protocol and quantified using PicoGreen assay (Thermo Fisher Scientific, Waltham, Mass.). 16S rDNA library preparation was performed according to Illumina's 16S Metagenomic Sequencing Library Preparation guide. The sequences for the 16S amplicon PCR forward and reverse primer were: 5'TCGTCGGCAGCGTCAGATGTGTATAAGA-GACAGCCTACGGGNGGCWGCAG and 5'GTCTCGTGGGCTCGGAGATGTGTATAAGA-GACAGGACTACHVGGGTATCTAATC C respectively. Sequencing was performed using Illumina MiSeq sequencer with Reagent Kit v2 and 500-cycle format to generate 2×250 base pairs (bp) paired-end reads.

A total of 11,498,568 reads were obtained for 43 samples with a median coverage of 54,127. Each paired-end reads were merged and assembled into a single read using the software PEAR with default settings. This yielded 11,434,008 assembled reads, resulting in 99.4% assembly rate. Assembled sequences with less than 350 bases or greater than 475 bases were discarded. All sequences from different samples were combined to create a single file. Redundant sequences were removed resulting 3,250,951 unique sequences. De-replicated sequences were sorted and clustered into operational taxonomic units (OTUs) based on minimal 97% identity using the UPARSE-OTU clustering algorithm. Chimeric sequences were detected and discarded using UCHIME (version 4.2.40). An OTU table was built with 952 OTUs.

Taxonomy assignment was performed using the kmer-based K-nearest neighbor search algorithm implemented in Mothur (version 1.39.5) by searching the reference sequence file from the Greengenes database (August 2013 release).

Sequence alignment was performed using PyNAST. Phylogenetic tree was built from the aligned sequences using FastTree. QIIME (version 1.9.1) functions were called for taxonomy assignment, OTU table and phylogenetic tree.

Putative bacterial metagenomic functions were imputed using PICRUSt, the Phylogenetic Investigation of Communities by Reconstruction of Unobserved States, on the 16S rRNA gene abundance data. The OTU table was normalized by dividing each OTU by the known or predicted 16S copy number abundances before metagenomic function prediction. The OTU table was normalized by calculating relative abundance, where each feature count was divided by the total sequence count in each sample and transformed in square root. Taxa with greater than or equal to 90% zeros or less than 0.01% relative abundance across all samples were removed.

Both alpha and beta diversity indexes were calculated in QIIME. The OTU table was first rarefied by subsampling the full OTU table to a depth coverage of 20,000 sequences per sample for 100 iterations. The Faith's phylogenetic diversity index was calculated for each subsampled OTU table and the sample mean for each metric was taken.

Differentially abundant Kyoto Encyclopedia of Genes and Genomes (KEGG) pathways were identified using the Linear Discriminant Analysis (LDA) Effect Size (LEfSe) software. Differentially abundant taxa were identified using a nonparametric rank test. Spearman's rank correlation coefficients were calculated between the key echocardiographic variables and the differentially abundant taxa.

Gut Microbial Diversity and Richness

Phylogenetic diversity (PD) is the phylogenetic analogue of taxon riches. Dogs in stage A have a distinguishable PD index than those in stage B1, B2, or C. Additionally, consistently, stage A dogs have a greater number of genera (116) than dogs at stage B1, B2, and C (99, 81, and 90 respectively).

Differentially Abundant Taxa

Four genera, *Erysipelatoclostridium*, *Ruminococcaceae* UCG014, *Butyricicoccus*, and *Faecalibacterium*, displayed higher abundances in the healthy stage A dogs than dogs with various stages of DMVD (Table 1). Interestingly, their abundances were inversely correlated with the size of left heart, indicating that as the heart enlarges, the bacterial abundances decrease.

TABLE 1

| Microorganism | Stage A* | Stage B1* | Stage B2* | Stage C* |
|---|---|---|---|---|
| *Erysipelatoclostridium* | 0.88 | 0.43 | 0.22 | 0.31 |
| Ruminococcaceae UCG014 | 0.29 | 0.05 | 0 | 0 |

TABLE 1-continued

| Microorganism | Stage A* | Stage B1* | Stage B2* | Stage C* |
|---|---|---|---|---|
| Butyricicoccus | 0.17 | 0.1 | 0 | 0 |
| Faecalibacterium | 1 | 0.05 | 0.06 | 0 |

*Normalized relative abundance

*Erysipelatoclostridium* abundance decreased as left ventricular diameter increased.

*Butyricicoccus* abundance inversely correlated with left atrial to aortic root ratio and left ventricular diameter.

*Faecalibacterium prausnitzii* abundance decreased as the left ventricular diameter increased.

*Ruminococcaceae* UCG014 (uncharacterized genus— https://www.arb-silva.de/browser/ssu/silva/X98011/) was highly abundant in the healthy dogs (stage A) when compared to dogs with DMVD. Abundance showed inverse correlations with left atrial diameter, left atrial to aortic root ratio and left ventricular diameter.

Metagenomic Function Prediction

Two metagenomic pathways, cardiolipin biosynthesis and valine degradation, were overabundant in dogs with stage B2 DMVD when compared to healthy stage A dogs, while glutamine/glutamate biosynthesis and tryptophan biosynthesis was underabundant in the healthy dogs when compared to B2 dogs.

Taken together, gut microbial diversity is higher in healthy dogs than in DMVD dogs. Four bacterial genera, *Erysipelatoclostridium, Ruminococcaceae* UCG014, *Butyricicoccus*, and *Faecalibacterium*, were more abundant in the healthy dogs than in DMVD dogs.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of diagnosing early stage degenerative mitral valve disease in a canine, the method comprising:
   obtaining a fecal sample from the canine;
   measuring a normalized relative abundance of a biomarker in the fecal sample, the measuring comprises extracting fecal DNA from the fecal sample, sequencing the extracted fecal DNA, and performing taxonomy assignment and sequence alignment of the sequenced fecal DNA, the biomarker selected from the group consisting of Erysipelatoclostridium, Ruminococcaceae UCG014, Butyricicoccus, *Faecalibacterium*, and combinations thereof; and
   determining that the canine has early stage degenerative mitral valve disease if the Erysipelatoclostridium is from 0 to 0.5 normalized relative abundance, the Ruminococcaceae UCG014 is from 0 to 0.1 normalized relative abundance, the Butyricicoccus is from 0 to 0.1 normalized relative abundance, or the *Faecalibacterium* is from 0 to 0.1 normalized relative abundance.

2. The method of claim 1, wherein the determining is based on two biomarkers.

3. The method of claim 1, wherein the determining is based on three biomarkers.

4. The method of claim 1, wherein the determining is based on all four biomarkers.

5. The method of claim 1, wherein the determining is based on Erysipelatoclostridium.

6. The method of claim 1, wherein the determining is based on Ruminococcaceae UCG014.

7. The method of claim 1, wherein the determining is based on Butyricicoccus.

8. The method of claim 1, wherein the determining is based on *Faecalibacterium*.

9. The method of claim 1, further comprising long-term administration on a regular basis of a therapeutically effective amount of a probiotic selected from the group consisting of Butyricicoccus, *Faecalibacterium* and combinations thereof to the canine having the early stage degenerative mitral valve disease.

* * * * *